United States Patent [19]
Paau et al.

[11] Patent Number: 5,194,258
[45] Date of Patent: Mar. 16, 1993

[54] PRODUCTION OF ENHANCED BIOCONTROL AGENTS

[75] Inventors: Alan S. Paau, Middleton; Mari L. Bennett, Stoughton; Lori L. Graham, Madison, all of Wis.

[73] Assignee: W. R. Grace & Co. - Conn., New York, N.Y.

[21] Appl. No.: 612,944

[22] Filed: Nov. 13, 1990

[51] Int. Cl.$^5$ .................... A01N 63/00; A61K 37/00; C12N 1/38; C12N 1/14
[52] U.S. Cl. ..................... 424/93 Q; 424/93 C; 435/244; 435/254
[58] Field of Search ............... 424/93, 93 Q, 93 C; 435/244, 254

[56] References Cited
U.S. PATENT DOCUMENTS

| | | | |
|---|---|---|---|
| 4,259,317 | 3/1981 | Vesley et al. | 424/93 |
| 4,438,593 | 3/1984 | McNew et al. | 424/274 |
| 4,489,161 | 12/1984 | Papavizas | 435/254 |
| 4,828,600 | 5/1989 | McCabe et al. | 71/76 |
| 4,877,738 | 10/1989 | Handelsman et al. | 435/252.5 |
| 5,041,290 | 8/1991 | Gindrat et al. | 424/93 |

FOREIGN PATENT DOCUMENTS 0226394 6/1987 European Pat. Off. .

OTHER PUBLICATIONS

Nelson et al. *Soil Biol. Biochem.* vol. 20(2) pp. 145–150, 1988.
Garraway et al. *Fungal Nutrition & Physiology* 1984, pp. 22–25.
Schroth and Hancock, "Disease-Suppressive Soil and Root-Colonizing Bacteria," *Science* 216:1376–1381, Jun. 1982.
Kommedahl, et al., "Variability in Performance of Biological and Fungicidal Seed Treatments in Corn, Peas and Soybeans," *Protection Ecology* 3:5561, 1981.
Levi, "Scientists Discover Biocontrol Solution to Root Rot," *CALS Quarterly*, p. 3, Summer/Fall 1987.
"Wisconsin Soil Bacteria Test Successful Against Root Rot," *Agrichemical Age*, p. 25A, Oct. 1987.
Roberts and Lumsden, "Effect of Extracellular Metabolites From Gliocladium-Virens on Germination of Sporangia and Mycelial Growth of Pythium-Ultimum," *Phytopathology*, pp. 461–465, 80(5), 1990. (Abstract).
Cho, Moon and Ha, "Biological Control of Fusarium-Oxysporum-F-Sp-Cucumerinum Causing Cucumber Wilt by Gliocladium-Virus and Trichoderma-Harzianum," *Korean J Plant Pathol*, pp. 239–249, 5(3) 1989 (Abstract).

Primary Examiner—Douglas W. Robinson
Assistant Examiner—L. Blaine Lankford
Attorney, Agent, or Firm—Quarles & Brady

[57] ABSTRACT

A method is disclosed for enhancing the biocontrol effect of microbial biocontrol agents used to combat fungal plant disease. The microbial biocontrol agent is fermented, formulated, or packaged in the presence of deactivated target pathogen such as a culture lethally heated pathogenic fungus. The treated biocontrol agent is enhanced in its activity by the contact with the inactivated pathogen.

7 Claims, No Drawings

PRODUCTION OF ENHANCED BIOCONTROL AGENTS

FIELD OF THE INVENTION

The present invention relates to the use of biological agents to combat plant diseases. In particular, the present invention relates to the inhibition of fungal diseases by enhanced microbial biocontrol agents.

BACKGROUND

Fungi are microscopic, spore-bearing eukaryotic organisms. Most fungal species are saprophytes, i.e. organisms that survive on dead organic matter, but some fungal species need living host animals or plants in order to grow. These fungal species may be parasites, which cause disease in the host organism, or they may exist in either a neutral or symbiotic relationship with a host plant.

More than 8,000 fungal species are parasites that can cause disease in plants. Mildew of roses, cereal rust and potato blight are commonly encountered examples of fungal diseases. Plant fungal diseases can have disastrous consequences for humans. For example, in the mid-1800s an epidemic of potato blight in Ireland caused the deaths of a quarter of a million people.

Damping-off and root rot are two fungal diseases that presently cause great economic damage to crop plants. One of the most common causative agents of damping-off is Pythium, a lower fungi and a member of the fungal class Oomycetes. Many other members of Oomycetes, for example, common water mold, potato blight, and downy mildew, are severe plant pathogens. Pythium, as other members of this class, lives in water or on moist soil, and is considered a saprophyte, even though its host organism may be living. Pythium infects crop seedlings at or below the soil surface when, under proper conditions, spores emerge from the Pythium vegetative body.

The disease of damping-off is found in almost every kind of vegetable, flower, cereal and tree and is found all over the world. The symptoms of the disease vary with the developmental stage of the plant when it is infected. In brief, when germinating seeds and seedlings are infected, the infected area becomes discolored and the infected tissue collapses. Older infected plants only have small lesions, but these lesions can girdle the plant and cause death.

Root rot is commonly caused by Rhizoctonia, a higher fungi. This fungus is parasitic on crops such as wheat, corn, stone fruits and forest trees. Rhizoctonia is a member of the subdivision Basidiomycetes, a subdivision of fungi which includes plant rusts, which are among the most destructive of plant diseases. Rusts have caused tremendous losses in wheat, oats, barley, bean, asparagus, cotton, and soybean. Basidiomycetes also includes species that cause smut in corn, oats, wheat, barley and rice.

Rhizoctonia causes root and stem rot on most annual plants throughout the world. The disease symptoms of root and stem rot are similar to those of Pythium-caused damping-off disease. Rhizoctonia exists primarily as a mycelium that consists of long cells with branches that grow at right angles to the main hypha.

The control of Rhizoctonia, Pythium and other plant diseases is a subject of great interest now. Manipulating soil conditions, such as dampness or aeration, is one means used to discourage fungal growth. Drenching the soil with chemicals, such as pentachloronitrobenzene, can reduce damping-off in seed beds. Certain fungicides, including contact and systemic fungicides, are effective. Recently, mulching fields with a layer of rice husks, or with photodegradable plastic, has been tried in an attempt to control Rhizoctonia and Pythium.

There are serious limitations inherent in all these fungal disease control methods. Application of chemical fungicides, even if effective, is expensive. Chemical buildup and runoff can accumulate in the environment and be detrimental to plant and animal life. Plants can become resistant to certain fungicides. Mulching fields is burdensome, and of questionable efficacy.

Currently, there is a great deal of interest in using microbiological control agents (biocontrols) against fungal plant disease. A biocontrol agent is an microorganism that, when added to soil, coated onto seeds, or in some other way introduced to the plant, greatly reduces plant disease incidence and severity. The mode of this disease control is often unknown. It may be because the biocontrol out-competes the pathogen for an ecological niche, because the biocontrol secretes or contains a substance that is toxic to the pathogen, because of parasitism of the biocontrol on the pathogen, or some combination of these or other effects.

Present biocontrols are perceived by some as not effective, reliable, and cost-efficient enough for present large-scale agricultural use. Schroth and Hancock, in a review article on biocontrols, state that "[c]onsiderable work must be done in such areas as developing a highly concentrated inoculum ... in a form that can be applied commercially." (Schroth and Hancock, "Disease-Suppressive Soil and Root-Colonizing Bacteria," *Science* 216:1376–1381, June, 1982.)

Several fungal species which are not pathogenic to plants have been found to be effective biocontrol agents. Examples of such fungal biocontrol agents may be found in U.S. Pat. No. 4,828,600 (Trichoderma species in corn) and U.S. Pat. No. 4,259,317 (Pythium species in sugar beets). Fungal species used as biocontrols against fungal pathogens may have advantages over bacteria. For example, a Penicillium species isolated from pea roots has been used to increase pea yield. (Kommedahl, et al. "Variability in Performance of Biological and Fungicidal Seed Treatments in Corn, Peas and Soybeans," *Protection Ecology* 3:5561, 1981.) Rhizoctonia is known to be controlled by several fungus species, such as species of Trichoderma, Gliocladium and Laetisaria. Biocontrol of plant fungal diseases is promising, but methods for improving the effectiveness of these biocontrol fungi are needed.

SUMMARY OF THE INVENTION

The present invention is summarized as a method of helping to protect crop plants from fungal pathogens by planting crops in the effective area of an enhanced biocontrol agent. The biocontrols used in the present invention are fungus species capable of enhancement by being cultured, formulated, or co-packaged in the presence of a deactivated pathogen.

It is an object of the present invention to enhance the growth of cultivated plants by providing enhancement of biocontrol agents.

It is another object of the present invention to protect cultivated plants from fungal pathogens.

It is another object of the present invention to provide a biocontrol with increased efficacy in actual agricultural and horticultural plant environmental conditions.

Other objects, advantages and features of the present invention will become apparent from the following specification when taken in conjunction with the accompanying claims.

DETAILED DESCRIPTION OF THE PREFERRED EMBODIMENT

The present invention is directed to a method of fostering plant growth by suppressing plant disease development. The method is characterized by the use of a biocontrol that has been cultured, formulated or co-packaged in the presence of deactivated pathogen. A biocontrol prepared in this manner is said to be "enhanced." The enhanced biocontrol is applied either to the soil into which the plant seed is sown, directly to the crop seeds, or directly to the plant in such a way that the effective area of protecting activity achieved by the biocontrol includes the vicinity of the crop seed or the resulting plant. The "effective area" of a protecting activity is that area in which the biocontrol organism is effective in helping to control the plant disease.

Selection and Growth of the Biocontrol

Biocontrols are bacterial or fungal species with an ability to control or restrain the growth of plant pathogens. The mechanisms of this control are often uncertain or unknown, and does not require characterization for the purposes of the present invention. Biocontrols suitable for use in this invention are fungus species capable of being "enhanced," or having increased efficacy, when exposed to a deactivated pathogen.

The examples describe the use of certain strains of *Gliocladium virens* and Trichoderma as biocontrol agents. These strains are known to control certain pathogenic fungi. It was decided to test this invention with biocontrol agents of known ability. It is not necessary, though, that the fungus species to be enhanced be a known biocontrol agent. Enhancement may increase the performance of an organism with marginal biocontrol ability to a significant amount. The examples below demonstrate a situation in which a fungal culture that exhibited no biocontrol ability above the control level when not enhanced, i.e. the Gliocladium B culture in Example 1, exhibited significant biocontrol ability when enhanced in accordance with the present invention.

The fungal culture is enhanced by being cultured with or exposed to whole deactivated pathogen. The pathogen is deactivated by rendering biologically incapable of pathogenic activity. One effective method for achieving deactivation is lethal treatment of the pathogenic fungus. In the examples below, deactivation was achieved by autoclaving a liquid culture of pathogen at 21 psi for 30 minutes at 123° C. However, deactivation of the pathogen may be performed in other ways, such as irradiation, chemical methods, or any means sufficient to render the pathogen incapable of normal reproduction or growth. The preferred method of working with the deactivated fungal culture is to filter the concentrate liquid culture through a simple paper filter, autoclave the matter retained by the filter, and add the autoclaved matter to the biocontrol fungal agents.

Because the enhancement of biocontrol agent activity is achieved when the biocontrol agent is exposed to a deactivated or dead pathogen, it seems likely that the interaction which results in the enhanced biocontrol activity is the result of an inducement or promotion of activity of the biocontrol fungi by some agent present on, or released by, the pathogenic agent. A possible source for such inducement could be a receipt present in the biocontrol agent activated by cell wall proteins or other molecules from the pathogen. It is to be understood, however, that this mechanism is at present poorly understood, and that while the enhancement effect can be demonstrated empirically, no claim is made to certain knowledge as to the specific mechanism underlying this phenomenon. What appears to occur, however, is that exposure to the fungal pathogen excites or induces the biocontrol to more effectively utilize whatever the mechanism is that hinders growth of the pathogen.

Culturing of the biocontrol fungus species can be done by standard fungal culture methods known to those in the art. Our preferred method is to grow the fungal cultures in a mixture of vermiculite and DY Broth (20 g dextrose and 10 g yeast extract per liter). The preferred ratio is 3 parts DY Broth to 2 parts vermiculite. For example, in a 12"×12" plastic bag, 2.4 lbs. of prepared DY Broth are mixed with 1.6 lbs. of vermiculite. The preferred vermiculite size is between 45 and 80 mesh. The mixture is sterilized and inoculated with a culture of the biocontrol agent. An inoculant of $10^2$–$10^3$ propagules into the bag can readily be achieved. After inoculation, the container is sealed tightly and left undisturbed at room temperature for approximately 11–15 days. Preferably, deactivated pathogen is added to the vermiculite/DY Broth mixture at a rate of 10 grams deactivated pathogen per pound of vermiculite/DY Broth mixture.

Selection of the Deactivated Pathogen

Example 1 demonstrates the increased efficacy of an enhanced biocontrol against the same pathogen used to enhance the biocontrol. In Example 1, a mixture of *Rhizoctonia solani* and *Pythium ultimum* is autoclaved and added to a fungal biocontrol agent, as described above. Rhizoctonia and Pythium were used as both target pathogens and deactivated pathogens in Example 1 to demonstrate the increased efficacy of an enhanced biocontrol in a situation where there is a single collection of known target pathogens. By "target pathogen" is meant the pathogen or pathogens, known or unknown, that threatens the crop plant. By "deactivated pathogen" is meant a deactivated pathogen used to enhance a biocontrol.

It is not necessary that the target pathogen and the enhancing pathogen be the same fungus species. Examples 2, 3 and 4 show the increased efficacy of biocontrol cultures enhanced with Rhizoctonia and Pythium against unknown pathogens. If a biocontrol with increased efficacy against an unknown soil pathogen is desired, the fungal pathogen could be cultured from the disease-producing soil by standard techniques, deactivated, and used to enhance a biocontrol. The exact identity of the pathogen, beyond that needed to determine culture conditions, need not be known.

Treatment of Seeds

To control target pathogens, plants must be cultivated within the effective area of the enhanced biocontrol. In the Examples below, seeds have been planted in soil mixed with enhanced biocontrols, at a dosage of up to $10^5$ propagules of enhanced biocontrol per gram of soil. Several other methods of introducing the enhanced biocontrol to the plant would be equally effective.

For example, the enhanced biocontrol could be fermented, formulated, or packaged in the presence of the deactivated pathogen. Then the enhanced biocontrol can be applied to the plant seed by dry or wet formulation and application to the seed. Alternatively, the enhanced biocontrol could be produced in an in-furrow formulation, wet or dry, which can be applied to the soil where the plant is to be raised. The enhanced biocontrol can even be applied as a spray, either in furrow during planting or to the soil after planting. What is required is that the enhanced biocontrol be placed by some means in the soil environment adjacent to the growing plant.

It is also envisioned that the exposure of the biocontrol to the deactivated pathogen can be shortly before or even contemporary with the application of the biocontrol agent. The biocontrol can be fermented in a culture medium, such as one based on a vermiculite carrier, and then the deactivated pathogen can be mixed with the fermented biocontrol agent as a part of its formulation or packaging process. Alternatively, the biocontrol and the deactivated pathogen can be produced separately and formulated and packaged in two separate compartments of a multi-part package. Then the biocontrol can be exposed to the deactivated pathogen either just before or during the application process. In particular, the use of this dual package approach, with exposure of the biocontrol to the deactivated pathogen just before application, will result in heightened enhancement of the biocontrol activity of the biocontrol agent.

The method of application will depend, to some degree, on the plants to be treated. For field crop plants where bulk materials are needed, exposure of the biocontrol to the deactivated pathogen during fermentation may prove more practical. For horticultural uses or for specialty crops, a co-packaging approach may be more acceptable to users and may result in the most effective control of the pathogen.

EXAMPLES

In the following Examples, the effectiveness of biocontrols enhanced in accordance with the present invention was demonstrated. As target pathogens, two fungal pathogens, known to cause root rot and damping-off, *Pythium ultimum* and *Rhizoctonia solani* were selected. To demonstrate the breadth of the fungus species that could be targets for enhanced biocontrols, target pathogens were chosen that represented both higher (Rhizoctonia) and lower (Pythium) fungi. The known pathogens Pythium and Rhizoctonia are used as target pathogens in Example 1. In Examples 2, 3 and 4, the target pathogens are unknown seed-borne and soil-borne pathogens.

As biocontrols, species of *Gliocladium virens* and Trichoderma were selected, both known to control Pythium and Rhizoctonia. In all examples, the biocontrols were enhanced over the controls by formulating them with a mixture of heat-deactivated *Pythium ultimum* and *Rhizoctonia solani*, in the manner discussed above. Thus, it was demonstrated that the enhanced biocontrol better protected the plants from known target pathogens than the controls, as shown in Example 1, and further that the enhanced biocontrol protected the plant from unknown pathogens, as shown in Example 2. Examples 3 and 4 demonstrate the utility of the enhanced biocontrols under actual field conditions.

EXAMPLE 1

Biocontrol of Cotton Fungal Disease Caused by Known Pathogens

Example 1 tested the effectiveness of enhanced biocontrols against known pathogens. To test the effectiveness of the biocontrols, the viability of cotton seeds planted in pathogen-infected soil was compared to the viability of cotton seeds planted in pathogen-infected soil with added biocontrols. To test the effectiveness of enhanced biocontrols, the viability of cotton seeds planted in pathogen-infected soil was compared when biocontrol agents were added in an enhanced and an unenhanced state.

Soil was mixed thoroughly with active plant pathogenic cultures of both *Pythium ultimum* and *Rhizoctonia solani*, two fungi known to produce damping-off and root rot in cotton. Each gram of soil was mixed with $3.4 \times 10^4$ pathogen propagules. This pathogen-infected soil was used in all the plantings in Example 1.

The plants were grown in a phytotron under conditions of high humidity and cool temperature (relative humidity=95%; photoperiod=12 hours/day; temperature during light periods=17°-20° C.; temperature during dark period=14°17° C.) Growing conditions were the same for all plants in Example 1.

As a control, 36 cotton seeds were planted in the pathogen-infected soil mixture. After 14 days, germinated seeds were counted. These seedlings were examined at various time intervals during the next 15 days and their survival rate was noted. As Table 1 indicates, none of the control seedlings were viable 29 days after planting.

*Gliocladium virens* and *Trichoderma fungi* were chosen as fungal biocontrol agents. These species were known to be effective in controlling root rot and damping-off. The biocontrols were cultured in a mixture of vermiculite and DY Broth, as described above. The mixture of vermiculite and nutrient was placed in containers, sterilized, and inoculated with the appropriate fungal culture. After inoculation, the containers were sealed tightly and left undisturbed at room temperature for approximately 15 days.

Liquid cultures of the pathogens *Pythium ultimum* and *Rhizoctonia solani* were filtered and autoclaved. Ten grams of the autoclaved matter was added per pound of vermiculite/DY Broth mixture inoculated with two strains of *Gliocladium virens* (strains GV6 and GL3) and called Gliocladium A.

The two *Gliocladium virens* strains (GV6 and GL3) were also formulated in a vermiculite/DY Broth mixture without added autoclaved pathogen. This fungal culture was called Gliocladium B.

Gliocladium A and Gliocladium B were each mixed with the pathogen-infected soil. The approximate amount of biocontrol used was $10^5$ propagules per seed. Thirty-six cotton seeds were planted in both Gliocladium A and Gliocladium B soil mixtures and allowed to germinate. As Table 1 indicates, after 29 days 8% of the seeds planted in Gliocladium A soil were viable. Seeds planted on Gliocladium B soil did not produce any viable seedlings.

A similar test was performed with the Trichoderma species. Three strains of Trichoderma (Th84, ATCC 24274, and ATCC 32247) were grown together in a vermiculite/DY broth culture. Autoclaved pathogen was added to the Trichoderma A vermiculite culture in the same manner as in the Gliocladium A culture. No autoclaved pathogens were added to the Trichoderma B culture. The Trichoderma A and B cultures were separately mixed with pathogen-enhanced soil. Thirty-six cotton seeds were planted in each soil mixture.

As Table 1 indicates, 19% of the seeds grown on soil mixed with Trichoderma A were viable after 29 days. No seeds planted in the Trichoderma B soil survived.

To summarize the results of Example 1, 8% of seeds planted in soil impregnated with an enhanced *Gliocladium virens* culture survived. 19% of the seeds planted in soil impregnated with an enhanced Trichoderma culture survived. Both survival rates are above those of seeds grown in soil without biocontrol agents or in soil with noninduced biocontrol agents.

TABLE 1

| Treatment | Percent Seedling Survival | | | | | |
|---|---|---|---|---|---|---|
| | 14 | 16 | 19 | 23 | 26 | 29 |
| | (days after planting) | | | | | |
| Control | 8 | 11 | 11 | 3 | 0 | 0 |
| Gliocladium A | 11 | 11 | 11 | 11 | 8 | 8 |
| Gliocladium B | 0 | 0 | 0 | 0 | 0 | 0 |
| Trichoderma A | 31 | 31 | 22 | 17 | 19 | 19 |
| Trichoderma B | 8 | 8 | 8 | 6 | 0 | 0 |

EXAMPLE 2

Biocontrol of Cotton Fungal Disease Caused by Soil-borne and Seed-borne Pathogens Examples 2(a) and 2(b) tested the effectiveness of induced biocontrols against unknown soil-borne and seed-borne pathogens. The growing conditions and biocontrol preparation in Example 2 are the same as those in Example 1, except that the planting soil used in Example 2 was not mixed with pathogens. Disease pressure was from natural, seedborne pathogens. Table 2 describes the results.

In Example 2(a), Gliocladium A and B cultures were mixed with soil. Thirty-six cotton seeds were planted in each mixture and in a control mixture that had no added biocontrol agents. After 14 days, germinated seedlings were counted. Viable seedlings were counted at various time intervals for a total of 54 days. Example 2(b) is a repeat of Example 2(a). In Example 2(b) the seedlings were examined for a total of 40 days.

As Table 2 indicates, in both example 2(a) and 2(b), more seedlings survived in Gliocladium A soil, which contained enhanced biocontrol agents, than survived in the Gliocladium B or control soil.

TABLE 2(a)

| Treatment | Percent Seedling Survival | | | | | |
|---|---|---|---|---|---|---|
| | 14 | 16 | 19 | 23 | 29 | 55 |
| | (days after planting) | | | | | |
| Control | 64 | 69 | 72 | 75 | 72 | 61 |
| Gliocladium A | 89 | 92 | 92 | 92 | 86 | 81 |
| Gliocladium B | 75 | 89 | 92 | 88 | 78 | 72 |

TABLE 2(b)

| Treatment | Percent Seedling Survival | | | |
|---|---|---|---|---|
| | 14 | 18 | 26 | 40 |
| | (days after planting) | | | |
| Control | 81 | 81 | 78 | 69 |
| Gliocladium A | 94 | 94 | 94 | 94 |
| Gliocladium B | 86 | 86 | 83 | 83 |

EXAMPLE 3

Biocontrol of Peanut Fungal Diseases under Field Conditions.

Example 3 tests enhanced biocontrol agents under field conditions. The test was performed during a growing season of approximately 5 months (April-September) in an agricultural field in Headland, Alabama. The test area was a 40 foot plot that was sown with 46 rows of peanut seeds.

As in Examples 1 and 2, the biocontrol fungi were grown in a vermiculite and DY Broth mixture and formulated with and without autoclaved pathogens *Pythium ultimum* and *Rhizoctonia solani*. In this example, Trichoderma was the sole biocontrol tested.

Peanut seeds were planted either in soil with no biocontrol agents, in soil with enhanced biocontrol agent (Trichoderma A) or in soil with unenhanced biocontrol agent (Trichoderma B). The vermiculite culture was applied to a seed furrow with an insecticide hopper at a rate of 3 pounds/acre. At the end of the growing season, the number of surviving plants in the furrows with enhanced and unenhanced biocontrol agents were compared to the number of plants surviving in the control furrow.

Table 3 lists the results as a percentage of plant survival as compared to control survival. 12.6% more plants survived in a furrow with enhanced biocontrol agent than survived in the control furrow. 2.9% less plants survived in a furrow with unenhanced biocontrols than survived in the control furrow.

TABLE 3

| Treatment | % Disease Control |
|---|---|
| Trichoderma A | 12.6 |
| Trichoderma B | −2.9 |

EXAMPLE 4

Biocontrol of Peanut Fungal Diseases under Field Conditions

Example 4 tests enhanced and unenhanced biocontrol agents under field conditions on peanut seeds treated with a fungicide. The test is done in an agricultural field in Headland, Ala., during a growing season of approximately 5 months (April to September). Peanut seeds were treated with Captan-DCNA (60-20), a chemical fungicide, at 4 oz/cwt. The test area was a 40 foot plot that was sown with 46 rows of peanut seeds.

Cultures of Trichoderma and *Gliocladium virens* were grown separately in a vermiculite and DY Broth mixture as in previous examples. The fungal cultures were formulated both with and without the autoclaved pathogens, *Pythium ultimum* and *Rhizoctonia solani*.

As before, Trichoderma A and Gliocladium A were the enhanced fungal cultures and Trichoderma B and Gliocladium B were the unenhanced cultures. As in Example 3, the fungal cultures were applied to seed furrows with an insecticide hopper at a rate of 3 lb/acre.

At the end of the growing season, the number of viable plants were counted. As reported in Table 4, 10.8% more plants survived in soil mixed with enhanced Trichoderma and 10.2% more plants survived in soil mixed with enhanced *Gliocladium virens* than survived on control soil. More plants survived in the soil mixed with enhanced biocontrols than survived in soil mixed with either unenhanced biocontrol agents.

TABLE 4

| Treatment | % Disease Control |
|---|---|
| Trichoderma A | 10.8 |
| Trichoderma B | −7.3 |
| Gliocladium A | 10.2 |
| Gliocladium B | 0.6 |

These results demonstrate that biocontrol agents may be enhanced in their efficacy of control of pathogenic fungal agents if the biocontrol agents are fermented with or exposed to the presence of inactivated pathogens. Because these results demonstrate this effect with biocontrol fungi and pathogenic fungi of such diverse types as illustrated here, one of ordinary skill in the art can readily understand that this method will be equally effective with other diverse biocontrol agents.

We claim:

1. A method of protecting crop plants from damping off or root rot caused by *Pythium ultimum* and *Rhizoctonia solani*, comprising:

(a) growing a culture of a biocontrol fungus which is capable of protecting the crop plants from root rot or damping off, the biocontrol fungus selected from the group consisting of Trichoderma, *Gliocladium virens* and a mixture thereof;

(b) culturing the biocontrol fungus with an effective amount of deactivated pathogen incapable of pathogenic activity selected from the group consisting of *Pythium ultimum, Rhizoctonia solani*, and a mixture thereof to enhance the biocontrol activity of the biocontrol fungus; and (c) applying the enhanced fungus to the cultivated plant to be protected or the locus thereof.

2. A method as recited in claim 1 wherein the applying step (c) is accomplished by coating the enhanced biocontrol fungi to the seed of the plant.

3. A method as recited in claim 1 wherein the applying step (c) is accomplished by applying the enhanced biocontrol fungi to the soil in which the plant is cultivated.

4. A method as recited in claim 1, wherein the deactivated pathogen is identical to the target pathogen.

5. A method as recited in claim 1, wherein the fungal culture is done in a mixture of vermiculite and a nutrient source.

6. A method as recited in claim 1, wherein the deactivated pathogen is autoclaved.

7. A method as recited in claim 1, wherein the enhanced fungal culture is mixed into the planting soil.

* * * * *